United States Patent [19]

Anderson et al.

[11] Patent Number: 4,521,254

[45] Date of Patent: Jun. 4, 1985

[54] CLEANING CONTACT LENSES WITH SOLUTION OF BROMELAIN AND CARBOXYPEPTIDASE

[76] Inventors: Ronald L. Anderson; Maria R. Mascio, both of 525 Sunbury Rd., Westerville, Ohio 43081

[21] Appl. No.: 346,013

[22] Filed: Feb. 5, 1982

Related U.S. Application Data

[63] Continuation-in-part of Ser. No. 232,392, Feb. 9, 1981, abandoned.

[51] Int. Cl.[3] .......................... B08B 3/08; C12N 9/48; C12N 9/50

[52] U.S. Cl. ........................................ 134/26; 134/42; 252/174.12; 252/DIG. 12

[58] Field of Search ............................... 134/1, 42, 26; 252/174.12, DIG. 12; 435/262, 264

[56] References Cited

U.S. PATENT DOCUMENTS

| | | | |
|---|---|---|---|
| 3,634,191 | 1/1972 | Laboureur | 435/264 |
| 3,720,402 | 3/1973 | Cummins et al. | 134/1 X |
| 3,910,296 | 10/1975 | Karageozian et al. | 134/42 X |
| 4,096,870 | 6/1978 | Manfuso | 134/42 X |
| 4,285,738 | 8/1981 | Ogata | 252/174.12 X |
| 4,323,467 | 4/1982 | Fu | 134/42 X |

FOREIGN PATENT DOCUMENTS

EPO5131 10/1979 European Pat. Off. .

OTHER PUBLICATIONS

Mihalyi, E., *Application of Proteolytic Enzymes to Protein Structure Studies', (1978), pp. 43-93.*

Coorman, W. M. et al., "Bromelain, Biochemical and Pharmacological Properties," *Pharm. Acta. Helv.*, 51, Nr. 4, (1976), 73, 112.

Spinell, M., *A Clinical Guide to Soft Contact Lenses,* (1979), pp. 3, 4, 13–15, 185, 186, 193–195.

Physician's Desk Reference, (1981), p. 1548.

Doi, E. et al., "Carboxypeptidase in Commercial Bromelain Power," *J. Biol. Chem.*, 1063, (1973).

*Primary Examiner*—Sidney Marantz

*Attorney, Agent, or Firm*—Porter, Wright Morris & Arthur

[57] ABSTRACT

A method and composition for the effective cleaning and treatment of soft, high water content, contact lenses, particularly the non-aphakic lens approved for general extended use and the aphakic lenses approved for prescribed use as a method of visual correction for the aphake. The method comprises immersing the lens in an aqueous solution which includes the protease, bromelain, as a principal ingredient and a further minor portion of carboxypeptidase enzyme, as the cleansing and treatment agent. The combination of bromelain and carboxypeptidase enzymatic agents produces surprisingly better cleansing results, in substantially shorter time, than either agent alone. The solution removes protein, mucin, lipid, calcium, mineral, and other physiologically encountered debris from the lens; and the lens so treated shows enhanced resistance to the accumulation of further deposits when subsequently worn by the patient.

13 Claims, 6 Drawing Figures

CLEANING CONTACT LENSES WITH SOLUTION OF BROMELAIN AND CARBOXYPEPTIDASE

FIELD OF THE INVENTION

This is a continuation-in-part of our co-pending application Ser. No. 232,392, filed Feb. 9, 1981, and entitled "Method and Solution for the Cleaning of Contact Lenses" now abandoned, and refiled on Oct. 20, 1982 as continuation application Ser. No. 435,474.

This invention relates to a cleansing solution and method for the removal of surface adhering and penetrating deposits of physiologically encountered debris which occur in the polymeric matrix of "soft" contact lenses. Such types of lenses are those which are worn for extended periods of time, and are known as "extended wear soft contact lenses"; however, the invention is as well applicable to daily wear soft contact lenses. Preferably, the invention is applicable to polymeric "soft" contact lenses having a normal water content greater than 38.6%.

BACKGROUND OF THE PRIOR ART

The initial development of the hydrophilic gel that comprises today's flexible lens occurred in 1960 in Europe by Professor Otto Wichterle and Dr. Drahoslav Lim. The importance of the structural similarity of the gel material to living tissue in eliminating the incompatibility between foreign body and tissue was stressed. The use of this material for contact lenses followed. Hydrophilic lenses became commercially available in Europe during the 1960's.

The Bausch and Lomb lens, "Soflens" was the first type of such soft contact lens to be approved by the Food and Drug Administration in the United States. The lens was approved for cosmetic purposes and served as the guideline for other lens manufacturers. A list of lenses approved by the FDA appears in the February 1980 issue of *Contact Lens Forum*. Aphakic lenses, such as the "Permalens" manufactured by the Cooper Co., Mountain View, Calif., the "Hydrocurve II" lens manufactured by Hydrocurve, Inc., San Diego, Calif., and the "Sofaulon" lens manufactured by Hydro Schulte are such types of lenses which have been approved by the FDA for aphakic patients and for cosmetic use. Such types of "soft" contact lenses are generally formed of a cross linked polymeric material capable of forming a three-dimensional matrix which permits water absorption, thereby allowing the lens to be applied to the eye.

The polymeric compositions used in such soft, high water content lenses include the following:

Polymacon (38.6% water): the homopolymer including hydroxyethylmethacrylate (which contains the hydroxy radical which makes the material hydrophylic) and ethylene glycoldimethacrylate (which acts as the cross-linking agent). The structure of the lens material is a three-dimensional network of chain-like macromolecules joined by cross-links. The HEMA unit forms the chains and ethylene glycoldimethacrylate forms the cross-links. The number of cross-links is small compared with the number of repeating units on the main polymeric chain.

Hefilcon A (45% water): the random copolymer of 2-hydroxyethylmethacrylate and N-vinyl-2-pyrrolidone. Ethylene glycoldimethacrylate forms the cross-links. There is approximately one cross-link for every seventy monomer units. The hydrophilic properties of the material are due to the free hydroxyl and carbonyl groups present in the structure.

Bufilcon A (45% water): a hydrophilic random copolymer of 2-hydroxyethylmethacrylate, N-(1, 1-dimethyl-3-oxobutll)-acrylamide, and methacrylic acid. The structure is a three-dimensional network of copolymer chains joined by trimethylolpropane trimethacrylate cross-links at a density of about one cross-link for every 1400 monomer units.

Tetrafilcon A (42.5% water): a random terpolymer of 2-hydroxyethylmethacrylate, N-vinyl-2-pyrrolidone, and methylmethacrylate. The polymer is a three-dimensional network of terpolymer chains joined by divinylbenzene cross-links.

Ocufilcon (46% water): 2-hydroxyethylmethacrylate and methacrylic acid cross-linked with ethylene glycoldimethacrylate.

Dimefilcon A (36% water): a hydrophilic copolymer of 2-hydroxyethylmethacrylate and methylmethacrylate, cross-linked with triethylene glycoldimethacrylate.

Vifilcon A (55% water): a soft hydrophilic copolymer of 2-hydroxyethylmethacrylate and povidone, USP. The chemical name is: Poly (2-hydroxyethylmethacrylate-co-ethylene dimethacrylate-co-methacrylic acid-g-povidone).

Droxifilcon (46% water): a random copolymer of 2-hydroxyethylmethacrylate and methacrylic acid modified with polyvinylpyrrolidone. The polymer is a three-dimensional network of copolymer chains cross-linked by triethylene glycoldimethacrylate.

Deltafilcon A (43% water): a cross-linked 2-hydroxyethylmethacrylate modified with isobutyl methacrylate.

Etafilcon A (43% water): a random copolymer of 2-hydroxyethylmethacrylate and methacrylic acid cross-linked with 1,1,1-trimethylolpropane trimethacrylate.

Phemecol or phemfilcon A (30% water): a cross-linked three-dimensional polymer network of 2-hydroxyethylmethacrylate and a small percentage of cross-linking monomers.

See: *A Clinical Guide to Soft Contact Lenses*, Spinell, M., 1979, at pages 13 et seq.

After the introduction of the soft lenses, it was noticed that deposits were being formed on the lenses. Patients had complained of lens discomfort and blurred vision. In most instances, the problem was remedied by fitting the patient with a new lens. This was an expensive and tedious solution to a cleansing problem. At approximately the same time, many laboratories initiated studies to determine the nature of the surface deposits that had formed on the lens after prolonged use. It had become apparent that the deposits needed to be identified in order to develop specific prophylactic or restorative techniques. Most of the studies revealed the predominant presence of proteins, especially lysozyme in such deposits; however, most of these same studies also revealed the presence of mucin, lipid, calcium, iron, and perhaps other debris.

In these studies, the findings differ as to the identification of the surface deposits. One particular study indicates that there are three different types of deposits: crystalline, proteinaceous, and granular. *A Clinical Guide to Soft Contact Lenses*, supra, at page 193. The primary source of the deposits are traceable to the tear constituents.

The proteinaceous deposits develop from constituents in the tear film that are secreted by the surrounding glands. They are solidified by heat in a low pH saline and bind with the actual lens material. An enzyme cleaner is available commercially from Allergan Pharmaceuticals, Irvine, Calif. which consists of papain enzyme and is useful in moderately removing this type of deposit. However, the use of a papain enzyme cleaner results in surface changes in the lens which, in turn, enhance the deposition of debris on further use of the lens.

The granular deposits, which actually grow into the lens matrix, have a gelatinous appearance. It is believed that these deposits result from a combination of stress, dryness, and lipid deposition.

Crystalline deposits are generally calcium or magnesium salts or other mineral type deposits and occur when a lens is stored in a high PH solution.

Hence, not only are such deposits adhesive to the surface of the lens, but such deposits also penetratingly adhere to the lens in a manner which may be characterized as a "growth" within the intestices of the polymeric matrix material from which the lens is formed.

Deposits which develop after use of a soft contact lens interfere with visual acuity and cause patient discomfort, ocular infection, and possibly allergic conjunctivitis. Deposits encourage dehydration, which in turn influences vision, comfort, and corneal integrity. The deposits also interfere with heat and chemical sanitization procedures. In this regard, it has been considered that although the majority of patients can wear extended wear contact lenses safely, the problem of calcium and protein deposits is a major stumbling block of long term successful wear of extended wear contact lenses.

Various cleansing solutions for soft contact lens care were developed to obviate the need for the wearer frequently to replace lenses because of the accumulations of debris on the lens. There are several solutions on the commercial market and several others are described in the patent and technical literature.

These solutions contain a variety of chemicals designed to aid in their primary function of cleansing. The additional chemicals may act as buffers, preservatives, and wetting agents. These constituents are present to create an optimum environment (pH) in which the chemicals can act, to keep the solution stable, to insure ocular comfort, or to disinfect the solution. Since soft lenses are hydrophilic, it is essential that the lens solution contain ingredients that will keep them wet and lubricated.

The cleansing solutions may be generally classed into detergents, surfactants, salines, hydraters, and special purpose cleaners. The literature, however, in describing the several solutions, emphasizes that none is completely satisfactory. See *A Clinical Guide to Soft Contact Lenses*, supra, at pages 185, 186 and 193–195.

There is described in U.S. Pat. No. 3,910,296 an aqueous solution for the cleaning of lenses containing a proteolytic enzyme, including the protease identified above as employed in a commercially available product, papain. Additionally, the solution described in the patent contains a non-toxic amount of a sulfhydryl group containing compound. A later filed and issued U.S. Pat. No. 4,096,870 discloses a similar solution using papain that is formulated into tablets using sodium chloride and boric acid as binding agents.

The enzymatic cleaner, papain, is a proteolytic enzyme derived from the dried and purified latex of the pawpaw tree. It is purported to be effective in removing moderate amounts of proteinaceous deposits from lens surfaces. A kit is commercially available from Allergan Pharmaceuticals, Inc. Irvine, Calif. that consists of two vials and a stabilized papain enzyme tablet. Such kits are provided for use with Bausch & Lomb "Soflens" polymacon contact lenses. In use of the kit, a specific amount of distilled water is poured in each vial and a tablet is allowed to dissolve therein. The lens is placed in the solution for six to twelve hours. It was noted that the solution took on the odor of hydrogen sulfide (rotten eggs). The lens when removed is washed off with saline. The saline may remove the milky white film that sometimes remains on the lens.

Although the papain enzymatic cleaner is an advance in the art, the advance is not sufficient. Initially, the effectiveness of the enzyme papain is limited to removing proteinaceous deposits but is not effective against non-proteinaceous deposits. Thus, although the proteinaceous deposits may be the predominant debris to be formed on the lens, the many studies have concluded that there is a significant amount of mucin, lipid, and calcium debris that will accumulate on the lens through prolonged use, and this debris is not removed by papain.

Another self-destructing factor found with the use of the enzyme papain is that in the process of removing surface deposits, the enzyme simultaneously creates new lens surfaces with small pits which actually encourage new deposit formations. That is, the pits are irregular and roughened to cause the debris to more readily adhere therein after the patient resumes wear of the cleansed lens.

SUMMARY OF INVENTION

It is an object of this invention to provide a method and composition for the effective cleaning and treatment of soft, high water content, contact lenses, particularly the non-aphakic lens approved for general extended use as a means of visual correction and the aphakic lenses approved for prescribed use as a method of visual correction for the aphake. The method comprises immersing the lens in an aqueous solution which includes (1) a principal portion of an endopeptidase, preferably bromelain, having an activity which results in an increase of permeability of a semipermeable membrane and (2) a further, minor, portion of an enzyme having an exopeptidase activity, preferably carboxypeptidase, combined together as the cleansing and treatment agent. The combination of enzymatic agents produces surprisingly better cleansing results, in substantially shorter time, than either agent alone. The solution removes protein, mucin, lipid, calcium, and other physiologically encountered debris from the lens, and the lens so treated shows an after-treatment characteristic of enhanced resistance to the accumulation of further deposits when subsequently worn by the patient.

The present invention is a preparation for, and a method of cleaning and treatment for, soft contact lenses, particularly, the high-water content lenses (in excess of 38.6% $H_2O$ content) to be approved by the FDA as general use non-aphakic lenses and aphakic use lenses. Representative types of such lenses include those polymeric matrix lenses described in the preceding portion of this application as well as such other high water content polymeric matrix lenses as may be available. The preparation of the invention includes a required amount of an endopeptidase, preferably bromelain and a further proportion of a second proteolytic enzyme, carboxypeptidase, combined in an aqueous solution. In the method of treatment, the lens is immersed in the aqueous solution of the bromelain/carboxypeptidase preparation for a shortened period of time for complete removal of all deposits on the lens. As a result, the lens is not only cleansed of both surface deposits and those other deposits which penetrate the three-dimensional polymeric matrix of the lens, but the lens also becomes treated to resist the further aggregation of surface and penetrating deposits. Optionally, the additional step of agitating or effervescing the solution by sonic or other types of generators may be used. Other chemicals in combination with the bromelain/carboxypeptidase solution, for the removal of specific deposits such as lipid and calcium have been considered. However, the results achieved by use of the composition alone allows such conventionally optional treatments to be considered unnecessary, except in the extreme circumstances. The results achieved by the combination of enzymatic compositions is unexpected in view of the activity of either composition alone and appears to be a surprising synergistic result achieved only when the combination of enzymes is used.

OBJECT OF THE INVENTION

It is a principal object of the invention to provide an enzymatic preparation, an aqueous solution thereof, and a method for the removal of deposits formed on the surface of soft contact lenses and those other deposits which penetrate the polymeric matrix of the lens material after prolonged wear. Preferably, the invention achieves optimum results when applied to a "soft" high water content (in excess of 38.6% $H_2O$) lens. And it is thus an objective of the invention to provide a high water content treated lens which is resistant to the aggregation of debris upon resumed use by the patient.

A further object of the invention is to provide a preparation, a solution, and a method that will remove aggregations and deposits from lenses irrespective of the nature of such deposits, and particularly in addition to protein deposits, such other deposits as mucin, lipid, iron, calcium, minerals, and other physiologically encountered debris.

Thus, the treatment preparations of the invention remove lens deposits regardless of their physiological or chemical nature and regardless of the physical or chemical manner in which such deposits became attached to the lens. In this regard, in the use of the invention, deposits are removed from soft contact lenses without altering the optical characteristics or parameters of the lens. Further, the lens is treated in a manner that enhances the resistance of the lens to the deposition of debris on further use of the lens by the patient.

Still other objects and features of the present invention will be understood and appreciated from a reading of the detailed description taken in conjunction with the figures in which:

DETAILED DESCRIPTION OF THE INVENTION IN CONJUNCTION WITH THE DRAWINGS

Figure 1:
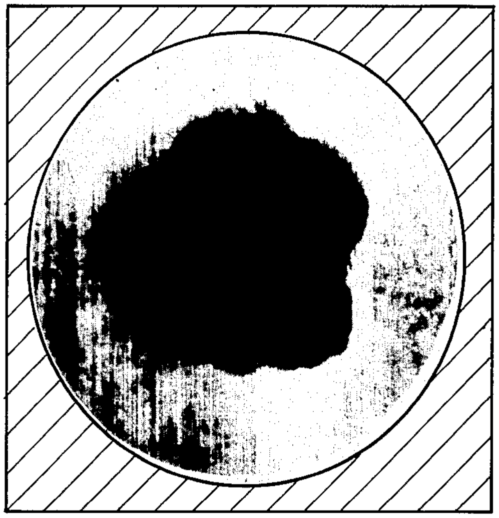
FIG. 1 is a photomicrograph of the surface of a lens having deposits thereon after use by a patient.

The invention comprises an enzymatic preparation, an aqueous solution thereof, and the use of the solution in a process for the cleaning and treatment of soft contact lenses; particularly the aphakic lens and the high water content nonaphakic lens approved by the FDA for general extended wear.

More particularly, the method and treatment described herein relates to the removal of debris which constitutes accumulated material which aggregates on the surface of, or penetratingly adheres within the polymeric matrix material of a soft contact lens of a type which preferably has a normal water content in excess of 38.6 percent. In general, in accord with the invention, the higher the water content of the lens treated, the better the results achieved.

As referred to above, the "accumulated material" which is referred to consists of the aggregation of compositions which become deposited upon, and within the three-dimensional matrix of the polymeric material of a soft contact lens, after a period of wear by the user. The relative proportion of the constituents of the deposits normally vary from patient to patient depending on individual physiology; and in the same patient may vary in proportion and character from time period to time period. However, it is known that the compositions in the deposits which are physiologically encountered in soft contact lenses include materials which can be described as proteinaceous, lipid, mucin, calcium, and other physiologic substances.

While the use of extended wear contact lenses in an aphake has been a great advance to ophthalmology, the use of such lens therapy has increased the medical cost of the person wearing the lens. These lenses are extremely fragile and have a high water content, and therefore collect, deposit on, or within the lens material, substances that are physiologically encountered in and around the eye. These deposits can be very irritating to the eye and therefore must be removed on a regular basis. While some of the proteins are relatively easily removed, the proteins which are tenacious can be removed in accord with the invention. The rate of deposit accretion for each patient wearing the extended wear lens is different. For example, some patients may go as long as six months without having any significant deposits on their lens, while others' lenses became deposited in as soon as two weeks after the placement of a brand new lens.

Such deposits shorten the useful life of the lens and irritate the eye. A tendency in the population of cataract patients who wear cataract correction contact lenses on a full-time basis is to develop surface deposits primarily from their own ocular secretions which severely shortens the life and usefulness of the lenses. Such deposits can be adequately cleaned in accord with the invention and the cost and need for replacement lenses can be eliminated.

The preparation utilized in the method and treatment of cleaning lenses of the present invention is a composition which includes proportions of bromelain, an endopeptidase, as the principal component and carboxypeptidase, an exopeptidase, as the subsidiary component, in combination, as the active cleansing agent. In this regard, in accordance with the invention, it is necessary that the bromelain include an additional proportion of, and be combined with, an amount of carboxypeptidase in the same solution to achieve the results of the invention. Neither enzyme alone will achieve comparable results. Bromelain is a proteolytic enzyme of the endopeptidase classification known for its pharmacological activity of increasing permeability of semi-permeable membranes. Carboxypeptidase is also a proteolytic enzyme, however, it is of the exopeptidase classification. While neither enzyme, by itself produces sufficient cleansing activity with respect to extended wear soft contact lenses, it has been found that in the combination, unexpected thoroughness in cleansing, as well as after-treatment characteristics which resist future depositions are achieved in many instances.

The properties of bromelain have been reported in the prior art, as generally related to its pharmacological activity. Bromelain is the collective name for the proteolytic enzyme found in tissues of the plant family "Bromeliaceae". Proteolytic activity in the juice of ananas was known prior to the turn of the century. The active substance was separated by salting out with ammonium sulphate. One of the early reports described the hydrolysis of albumin and carbobenzoxy derivatives by bromelain. Thereafter, the investigations concerned the heterogeneity of bromelain enzymes. The properties of one or more proteolytic enzymes occurring in "Ananas comosus var. Cayenne" was noted. Electropheric separation of the protein, inorganic materials and complex carbohydrate materials resulted in five to eight different peaks. The three main peaks corresponded respectively with a protease with basic isolectric point, a protease with an acid isoelectric point, an acid phosphatase and a labile peroxidase. The bromelain preparation was active against a variety of proteinaceous substrates such as denatured egg albumin, blood albumin, hemoglobin, and N-benzoylarginine amide. In the prior art, it has also been reported that a bromelain preparation also contained seven protease inhibitors active against bromelain, papain, and ficin. These inhibitors are proteins. The preparation was also activated by reducing agents and inhibition with heavy metals; however, no inhibition occurred with N-ethylaleimide. Also, literature reveals that the catalysis of ester and amide substrates by bromelain differs from the hydrolysis by papain. It has also been shown that bromelain was found to have a significant anti-edema effect by crossing semipermeable membranes. The reduction of edema was significantly greater than after treatment with papain, ficin, and trypsin. Bromelain is prepared from the extracted juice by precipitation of the enzyme with acetone, ammonia sulphate, or alcohol. Its activity is greatest at a pH ranging from three to four. Bromelains, as an anthelmintic became known because of its power to digest living worms.

Caseinolytic activities of commercial bromelains, ficin, and papain are similar, however, the significant difference between these similar enzymes is the hydrolyzing activity found in certain kinds of bromelains because of a proteolytic enzyme other than bromelain—the pineapple carboxypeptidase, which is encountered as an impurity in certain commercial preparations of bromelain.

In contrast, carboxypeptidase is classified as a different type of protease according to the site of attack of the enzyme. Thus, whereas bromelain is considered to be an endopeptidase, carboxypeptidase in an exopeptidase. E. Mihalyi, *Application of Proteolytic Enzymes to Protein Structure Studies*, 2d ed Vol. I, CRC Press, Inc., West Palm Beach, Fla. 1978, Table 6, page 48.

When the activities of the two enzymes are combined in connection with the method herein for the treatment of soft contact lenses having a high water content, it has been found that surprisingly better results in efficiency and character are achieved when compared with respect to either the prior art papain cleanser or to test results achieved when either bromelain or carboxypeptidase is used alone as a cleansing agent.

Thus, in the present application, we describe our highly effective process for removing the majority of deposits and aggregations which are physiologically encountered in extended wear "soft" contact lenses. Since the lenses are quite clear, in most cases where deposited material affects visual acuity and/or causes discomfort, the lens treated in accord with the invention can be re-used. After treatment, improvement in visual acuity, and freedom from the irritating discomforts of deposited material results. The need for replacement lenses is negated. Further, in certain instances an after treatment characteristic of enhanced resistance to further deposits results when a lens is treated with the bromelain/carboxypeptidase compositition of the invention.

Since the expense of the cleaning procedure of the invention can be up to less than 25 percent of the cost of a new extended-wear lens, use of the invention will considerably decrease the net cost to the patient and/or insurance companies which cover costs of lens replacement in patients requiring such lenses. Since, the national average of contact lenses replaced are reported to be two to three contacts per year, the evident economic value of the invention as well, as its therapeutic benefit, can readily be appreciated.

The invention is explained, and the advantages achieved are set forth in the following examples:

EXAMPLE I

A.

Several hundred lenses of the aphakic type and of the general extended wear non-aphakic type were provided by medical doctors for cleaning. The lenses were worn by patients for an extended period of time—some three months or longer. In some instances, prior unsuccessful attempts were made to clean the lenses with a commercially available papain enzyme cleaner. The cleaning process included a step by step microphotograph for a substantial number of lenses. In each instance of cleaning the lenses, continual periodic examination of the lens under a microscope provided the needed information as to the time necessary for the complete cleaning of the deposits from the lenses. The length of the cleaning process for any particular lens was directly dependent on the amount and severity of the deposits on the lens.

B.

200,000 Rorer units or 1 gram of bromelain was suspended in 30 cc of distilled water. The resultant suspension was placed in a 35 cc borosilicate glass vial.

The bromelain preparation employed was derived from the enteric coated tablet "Ananase - 100" (Registered Trademark) manufactured by William H. Rorer, Inc., 500 Virginia Drive, Fort Washington, Pa. 19034. The activity of one Rorer Unit of protease activity is defined as that amount of enzyme which will so hydrolyze a standardized casein substrate at pH 7.0 and 25° C. as to cause an increase in absorbance at 280 mm. of $1\times10-5$ per minute of time. *Physician's Desk Reference*, page 1548, 1981.

The vial, in turn, with the lens to be cleaned therein was placed in a multi-phase ultrasonic scrubber of commercial design. The vial was subjected to the ultrasonic agitation for 5 minutes every 2 hours. This process continued until all the deposits were removed from the lens. The sonic agitation was limited to periods of 5 minutes in that the water needed to be maintained at 50 degrees Celsius. The time period before complete cleansing occurred was in the range of 24 to 72 hours depending upon the severity of the deposits involved.

As aforesaid, the lens was examined under a microscope after each 5 minute agitation, and the step continued until all the debris was removed.

The multi-phasic ultrasonic generator was shown to have no physical affect on the lens, whereas, the single-phase ultrasonic generator showed evidence of damage to the lens.

While the suspended solution containing the lens to be cleaned need not be agitated, in the absence of agitation, however, the time period for soaking needed to be increased before all of the debris is removed.

A solution of bromelain and other ingredients known to assist in the removal of deposits other than protein, such as lipolytic enzymes was prepared. The results of this combination of the foregoing ingredients were unsatisfactory. Further experimentation which consisted of eliminating the other ingredients one by one had no noticeable effect in improving or diminishing results.

Figure 2:
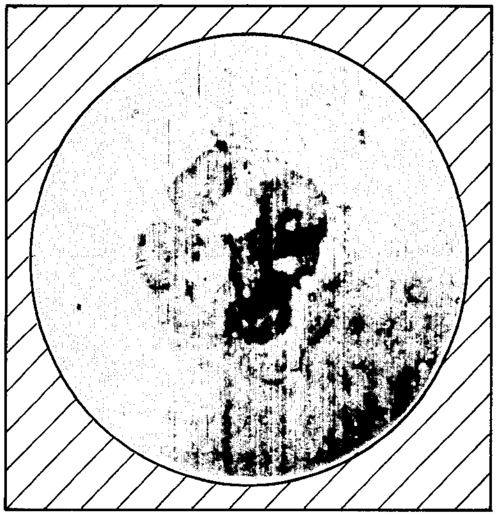
FIG. 2 is a photomicrograph of the lens of FIG. 1 after having been cleaned and treated with an enzyme cleanser and mechanical abrasive manipulation.

With particular reference to the drawings, that is, the microphotographs of FIGS. 1 and 2, there is shown a soft lens (permalens-Cooper) that had been worn by a patient continuously for approximately three months. This specific lens was identified by the referring medical doctor as one of the worst lenses he had seen relative to the accumulation of debris. The lens was no longer wearable by the patient. FIG. 1 depicts this lens prior to any contact with the solution, that is, as received. FIG. 2 shows the same lens after the cleaning operation was completed. Treatment of this specific lens shown in the figures required a time period of 14 hours, when periodic scrubbing of the lens with "Morton's Popcorn Salt" which consists of very fine granules of sodium chloride was additionally provided. During the period of treatment, the bromelain solution was changed every 4 hours, and in total three times. The lens was restored as much as possible to its original condition; the patient has continued to wear this lens following treatment. Practitioner and patient were completely satisfied. The debris was completely removed irrespective of its nature or make-up. The globular appearance on the cleansed lens of FIG. 2 is simply a light reflection and not residual deposits. It was considered that, at best, a cleaning operation involving a bromelain solution and agitation or scrubbing would require approximately eight to ten hours to achieve satisfactory results.

It was concluded that the procedure of this Example I, and the use of the bromelain preparation by itself was effective. Although, after approximately four hours, the suspended bromelain solution broke down and needed to be replaced with a fresh solution, and mechanical abrasion with fine sodium chloride salt crystals was required to complete the removal of all deposits, the process nevertheless performed significantly better than the prior art papain cleanser.

EXAMPLE II

The procedure of Example I was repeated with commercial papain cleaner with other lenses having equivalently severe deposits. Even with an extended period of soak, and the ancillary use of ultrasonic agitation, papain could not achieve satisfactory cleansing results regardless of the length of time of treatment.

Use of the commerical papain solution resulted in the finding that papain acitivity is limited to the removal of protein; Further, as is also reported in the literature, the after effect of use of the papain solution is that pits are left in the lens after the lens is cleaned of the minor surface deposits which papain is able to remove. The presence of the pits enhances the accumulation of other debris which papain cannot satisfactorily remove when the lens is again worn by the patient.

In contrast, the solution utilizing bromelain also leaves pits in the lens; but unlike papain, the pits are completely cleansed of debris thereby leaving behind no binding site to which "new" protein or other materials may easily adhere. Lenses once cleaned, and thereafter worn for a period of time, which were returned again for cleaning by the bromelain solution showed accumulation of debris adjacent to the pits but not within the pits.

On second and repeated cleansings of the same lens after intervals of wear by the patient, continued studies were made of microphotographs to determine why the pits in the lens cleaned with papain left debris, while the lens cleaned with bromelain resisted further accumulation of debris on areas previously cleaned. Whether the residue examined was protein, for which the literature notes papain is only moderately effective, or the residue consisted of other types of debris which the users of papain acknowledge cannot be removed with papain, is not known particularly at this time. It is known, however, that the bromelain solution of the invention does remove all deposits and remaining pits are completely cleansed. In this regard, it is believed with sufficient justification that the bromelain solution of the invention penetrates the lens to a considerable depth-considerably greater than the solution containing papain.

EXAMPLE III

A commercial bromelain powder including a proportion of carboxypeptidase was employed to the prepare a lens soak solution (0.5 grams bromelain per 7 cc of distilled water). Such a powder was a commercial bromelain preparation (having a natural "impurity" component of carboxypeptidase) sold and distributed by Sigma Chemical Company, St. Louis, Mo. 63178. A separate solution was also prepared from a purified bromelain powder in the proportion of 200,000 Rorer units bromelain to 50 micrograms purified carboxypeptidase in about 7 cc of distilled water.

The separate carboxypeptidase was a preparation from bakers yeast and was a Lyophilized powder containing approximately 20% protein; balance Citrate buffer, pH approximately 5 and also contained Amidase and Esterase activities.

The surprising discovery of the preparation, solution and method of Example III for lens treatment is that the combination of a bromelain active enzyme in a water solution including the presence of a carboxypeptidase active enzyme achieves a result in cleansing and treatment with respect to soft contact lenses having a water content in excess of 38.6 percent which is unexpected in view of the results achieved by either component individually. Further, while it had been previously reported in the literature that carboxypeptidase was a proteolytic enzyme assumed to be present (as an impurity) in occasional minor quantities in commercial bromelain powder derived from the pineapple stem, the surprising result achieved by the deliberate combination of the two types of enzymes in connection with cleansing and treatment of "soft" contact lenses having a water content in excess of 38.6 percent has not heretofore been realized. See, for example, Doi, E., et al., "Carboxypeptidase in Commerical Bromelain Powder" *J. Biol, Chem.*, 1063 (1973). Effective results are achieved in accord with the combination of the invention whether the "combination" of carboxypeptidase with bromelain occurs as a natural impurity in the bromelain or whether the bromelain and carboxypeptidase are deliberately synthesized.

Figure 3A:
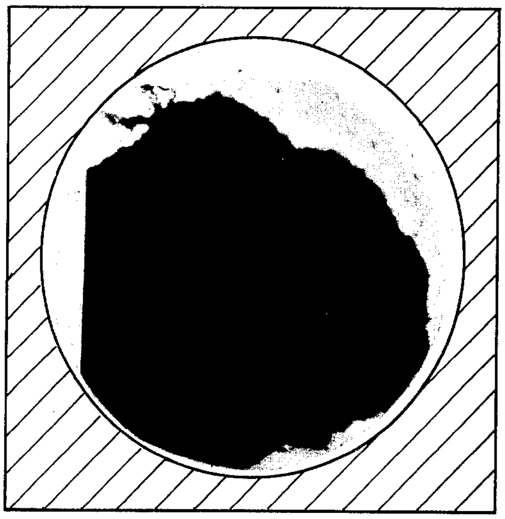
FIGS. 3A, 3B, 3C and 3D show in sequence the surprisingly quick and effective cleansing of the lens which is achieved by the combined enzyme preparation of the invention.
Figure 3B:
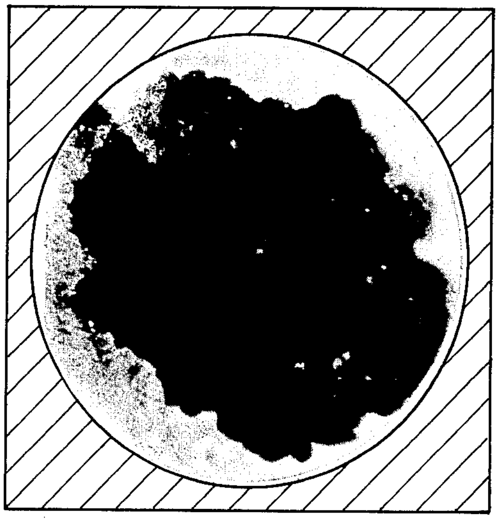
Figure 3C:
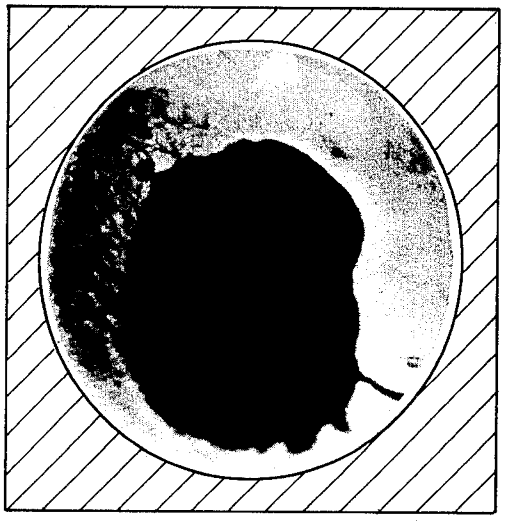
Figure 3D:
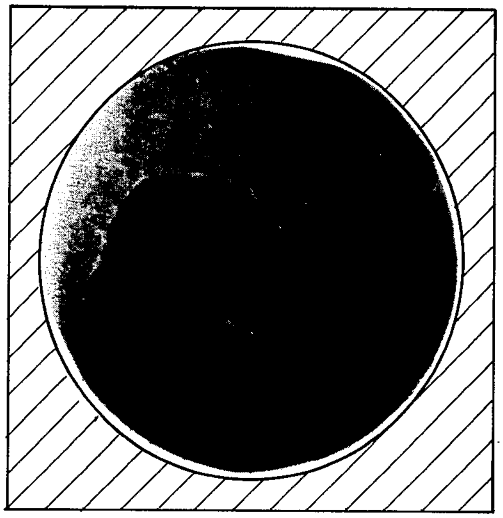

This surprising effect is illustrated by the sequence of FIGS. 3A through 3D. FIG. 3A shows a soft, high water content, polymeric matrix lens of the same type referred to in Example I, as received, having significant deposits and debris accreted thereon. The same lens is shown in FIG. 3B after four hours soaking at 50° C. with 200,000 Rorer units of Bromelain in 7 cc of distilled water. Only slight improvement is shown. The lens was placed in a new solution of 200,000 Rorer units Bromelain to which was added 50 mg. carboxypeptidase in 7 cc distilled water at 50° C. After only two hours, as shown in FIG. 3C, the lens was approximately 50% cleansed, and after two additional hours (four hours total in the same solution), the lens was entirely cleansed of debris and approved for shipment back to the patient. Essentially, similar results of fast (less than four hours) and effective cleansing of soft contact lenses are achieved when the bromelain/carboxypeptidase solution is used at temperatures of 50° to 70° C., and it does not appear to affect results if the carboxypeptidase component of the solution is the naturally occurring "impurity," or is a separately formulated proportion included in a "pure" bromelain solution. A further advantage of the combined bromelain/carboxypeptidase solution is that the solution need not be changed during a cleansing cycle, as was required when bromelain alone was used as described in Example I.

In this regard, in connection with the formulation of the invention the preferred proportional range of the respective enzymatic ingredients is approximately 10 parts by weight bromelain to approximately 1 part by weight carboxypeptidase in solution together in a solution of approximately 6 to 15 cc distilled water. Room temperature is satisfactory for the treatment solution, although heating to 50 to 70 degrees Celsius will expedite the cleansing.

In most instances, a high water content lens is completely cleaned and treated in four hours at room temperature (55°-75° F.) without agitation or other physical manipulation. This is a significant and unexpected improvement in the cleansing of high water content lenses when compared with prior art cleansing procedures which require 18 hours immersion of the lens, solution changes, physical manipulation, or abrasive treatment with salt to remove equivalently severe deposits. Further, thorough cleansing and better after-treatment properties of the cleansed lens are achieved when the bromelain/carboxypeptidase composition is employed.

While the absolute proportions of bromelain to carboxypeptidase, the relative concentration of the enzyme solution, and the temperature and time of treatment may vary as matters of choice, the critical finding is that the surprising results of shortened time and cleansing effectiveness are achieved in instances, regardless of other parameters, only when a proportion of carboxypeptidase is included with a proportion of bromelain.

Commercial preparations of bromelain and carboxypeptidase which do not contain additives or preservatives such as N-ethylmaleimide or di-isopropyl-gluorphosphate, are preferred.

Following cleansing and treatment in accord with the invention, a post-treatment consisting of an after-soak in distilled water is used to wash the lens of enzymatic material, and the lens may be placed in a normal saline solution so that it is physiologically acceptable for wear by the patient.

The treatment has been shown to be safe and effective. Furthermore, this method serves to restore lenses that previously would had to have been replaced, costing the consumer, Medicare, or insurance agencies valuable funds better directed elsewhere.

In summary, the composition, solution and method of the invention provides salutary therapeutic effects and achieves considerable economic benefit in the treatment of various ophthalmic conditions where soft contact lenses are used or required. Use of the foregoing invention will prolong the useful life of a high water content soft contact lens formed from a polymeric matrix material, thus reducing the patient's expense involved in contact lens replacement in addition to providing the therapeutic benefit of enhancing the lens' resistance to further deposition in most, approximately 80%, of the cases.

What is claimed is:

1. The method of treating an extended wear contact lens by removing surface deposits and penetratingly adhering aggregations of physiologically encountered debris from said lens comprising:

(a) soaking the lens in an aqueous solution which comprises a principal proportion of bromelain active enzyme and an additional proportion of carboxypeptidase active enzyme suspended in the same aqueous solution and controlling said soaking for a period of time sufficient for the removal of all of the debris from said lens;

(b) rinsing said lens with a separate solution of distilled water; and (c) placing said lens in a normal saline solution; whereby, said lens becomes cleansed of said deposits and debris.

2. The method of claim 1 wherein (a) the principal portion of bromelain in said solution comprises approximately 200,000 Rorer units of bromelain; (b) the minor proportion of carboxypeptidase is a minor proportion which comprises approximately 50 micrograms; and (c) said portion of bromelain and carboxypeptidase are present per each 6 to 15 cc. of water.

3. The method of claim 1 of claim 2 in which the temperature of the solution is approximately 50° to 70° C.

4. The method of claim 1 wherein the deposits and debris include an aggregation of proteinaceous, lipid, mucin, and calcium material.

5. The method of claim 1 in which one or more of the surface deposits and aggregations of debris is a composite debris.

6. The method of claim 1 in which the period of soaking is less than approximately 4 hours.

7. The method of claim 1 in which the lens is a soft lens and has a normal high water content.

8. The method of claim 7 in which the normal water content of the lens is in excess of 38.6%.

9. The method of claim 8 in which the period of soaking is less than approximately four hours.

10. A lens cleaning composition for the removal of surface deposits and physiologically encountered debris from a high water content soft contact lens formed from a polymeric matrix material, said cleaning composition including: a principal portion of an enzyme having an activity of increasing permeability of semi-permeable membranes and a minor portion of a carboxypeptidase active enzyme.

11. The composition of claim 10 in which the enzyme having an activity of increasing permeability of semi-permeable membranes is a bromelain.

12. The composition of claim 11 in which the portion of bromelain is equivalent to approximately 200,000 Rorer units and the portion of carboxypeptidase is equivalent to approximately 50 micrograms purified carboxypeptidase.

13. A contact lens cleaning solution being a suspension in distilled water of the composition of claim 10, claim 11, or claim 12.

* * * * *